US009576876B2

(12) United States Patent
Sung et al.

(10) Patent No.: US 9,576,876 B2
(45) Date of Patent: Feb. 21, 2017

(54) ORGANIC-INORGANIC HYBRID THIN FILM AND METHOD FOR PRODUCING THE SAME

(71) Applicants: IUCF-HYU (INDUSTRY-UNIVERSITY COOPERATION FOUNDATION HANYANG UNIVERSITY), Seongdong-gu (KR); BASF Coatings GmbH, Muenster (DE)

(72) Inventors: Myung Mo Sung, Seocho-gu (KR); Kyu Seok Han, Yeongdeungpo-gu (KR)

(73) Assignees: BASF Coatings GmbH, Muenster (DE); IUCF-HYU (Industry-University Cooperation Foundation Hanyang University), Seongdong-gu (KR)

( * ) Notice: Subject to any disclaimer, the term of this patent is extended or adjusted under 35 U.S.C. 154(b) by 67 days.

(21) Appl. No.: 14/413,754

(22) PCT Filed: Nov. 4, 2013

(86) PCT No.: PCT/KR2013/009909
§ 371 (c)(1),
(2) Date: Jan. 9, 2015

(87) PCT Pub. No.: WO2015/030297
PCT Pub. Date: Mar. 5, 2015

(65) Prior Publication Data
US 2016/0276241 A1    Sep. 22, 2016

(30) Foreign Application Priority Data
Aug. 30, 2013 (KR) .................. 10-2013-0104463

(51) Int. Cl.
*H01L 51/40* (2006.01)
*H01L 23/31* (2006.01)
(Continued)

(52) U.S. Cl.
CPC ............ *H01L 23/3192* (2013.01); *C07F 3/06* (2013.01); *C07F 5/063* (2013.01);
(Continued)

(58) Field of Classification Search
None
See application file for complete search history.

(56) References Cited

U.S. PATENT DOCUMENTS 6,866,949 B2    3/2005    Ota et al.
7,229,703 B2    6/2007    Kawashima et al.
(Continued)

FOREIGN PATENT DOCUMENTS

CN    102027603 A    4/2011
JP    5-220106 B2    8/1993
(Continued)

OTHER PUBLICATIONS

Jens Meyer, et al; Al2O3/ZrO2 nanolaminates as ultrahigh gas-diffusion . . . ; Advanced Materials; 2009; vol. 21; pp. 1845-1849.
(Continued)

*Primary Examiner* — Jack Chen
(74) *Attorney, Agent, or Firm* — Oblon, McClelland, Maier & Neustadt, L.L.P.

(57) ABSTRACT

The present invention relates to an organic-inorganic hybrid thin film and a method for preparing the same and more specifically to an organic-inorganic hybrid thin film including a stable new functional group and a method for preparing the organic-inorganic hybrid thin film that is formed by the
(Continued)

molecular layer deposition method alternately using inorganic precursor and organic precursor.

17 Claims, 19 Drawing Sheets

(51) Int. Cl.
| | |
|---|---|
| *G02F 1/1333* | (2006.01) |
| *C23C 16/455* | (2006.01) |
| *H01L 31/0203* | (2014.01) |
| *H01L 51/00* | (2006.01) |
| *H01L 51/52* | (2006.01) |
| *C07F 3/06* | (2006.01) |
| *C07F 5/06* | (2006.01) |
| *H01L 21/56* | (2006.01) |
| *H01L 23/29* | (2006.01) |

(52) U.S. Cl.
CPC .. *C23C 16/45529* (2013.01); *C23C 16/45553* (2013.01); *G02F 1/1333* (2013.01); *G02F 1/133305* (2013.01); *H01L 21/563* (2013.01); *H01L 23/293* (2013.01); *H01L 31/0203* (2013.01); *H01L 51/005* (2013.01); *H01L 51/0034* (2013.01); *H01L 51/0096* (2013.01); *H01L 51/5253* (2013.01); *G02F 2001/133302* (2013.01); *G02F 2202/022* (2013.01); *H01L 2251/301* (2013.01); *H01L 2251/305* (2013.01); *H01L 2251/308* (2013.01); *H01L 2251/558* (2013.01)

(56) References Cited

U.S. PATENT DOCUMENTS

| | | |
|---|---|---|
| 7,378,157 B2 | 5/2008 | Sakakura et al. |
| 7,442,428 B2 | 10/2008 | Kawashima et al. |
| 7,709,097 B2 | 5/2010 | Agata et al. |
| 7,791,275 B2 | 9/2010 | Oosono et al. |
| 7,812,530 B2 | 10/2010 | Handa et al. |
| 7,947,377 B2 | 5/2011 | Kishimoto |
| 7,951,458 B2 | 5/2011 | Ogura et al. |
| 8,057,904 B2 | 11/2011 | Murakami et al. |
| 8,067,085 B2 | 11/2011 | Aiba |
| 8,124,179 B2 | 2/2012 | Nilsen et al. |
| 8,197,942 B2 | 6/2012 | Sakakura |
| 8,241,749 B2 | 8/2012 | Kano et al. |
| 2005/0153077 A1 | 7/2005 | Gedeon et al. |
| 2006/0062995 A1 | 3/2006 | Yamamoto |
| 2008/0102313 A1 | 5/2008 | Nilsen et al. |
| 2009/0061223 A1 | 3/2009 | Tsukahara et al. |
| 2009/0163670 A1 | 6/2009 | Aoshima et al. |
| 2010/0178481 A1 | 7/2010 | George et al. |
| 2011/0052891 A1 | 3/2011 | Takahashi et al. |
| 2011/0281106 A1 | 11/2011 | Kishimoto |
| 2012/0121932 A1 | 5/2012 | George et al. |
| 2012/0276353 A1 | 11/2012 | Nakatsugawa |
| 2013/0017400 A1 | 1/2013 | Imai et al. |
| 2016/0276241 A1* | 9/2016 | Sung .................. H01L 23/3192 |

FOREIGN PATENT DOCUMENTS

| | | |
|---|---|---|
| JP | 2008-255242 A | 10/2008 |
| KR | 10-2007-0095919 A | 10/2007 |
| TW | 201246578 A | 11/2012 |
| WO | 2009002892 A1 | 12/2008 |

OTHER PUBLICATIONS

Mika Vaha-Nissi, et al; Barrier properties of Al2O3 and alucone coatings and . . . ; Thin Solid Films; 2012; vol. 520; pp. 6780-6785.
Seung-Woo Seo, et al; Bending properties of organic-inorganic multilayer . . . ; Thin Solid Films; 2014; vol. 550; pp. 742-746.
Kwan-Hyuck Yoon, et al; Fabrication of a new type of organic-inorganic hybrid . . . ; Nanoscale Research Letters; 2012; 7.
Arrelaine A. Dameron, et al; Gas diffusion barriers on polymers using multilayers . . . ; J. Phys. Chem. C; 2008; vol. 112; pp. 4573-4580.
Jin-Hwan Choi, et al; Highly conformal SiO2/Al2O3 nanolaminate gas-diffusion . . . ; Nanotechnology; 2010; vol. 21; pp.
G.L. Graff, et al; Mechanisms of vapor permeation through multilayer barrier . . . ; Journ. Applied Physics; 2004; vol. 96; No. 4; pp. 1840-.
Byoung H. Lee, et al; Monolayer-precision fabrication of mixed-organic-inorganic . . . ; Organic Electronics; 2008; vol. 9; pp. 1146-1153.
Byoung H. Lee, et al; Rapid vapor-phase fabrication of organic-inorganic hybrid . . . ; J. Am. Chem. Soc.; 2007; vol. 129; pp. 16034-16041.
Jin-Seong Park, et al; Thin film encapsulation for flexible AM-OLED: a review; Semicond. Sci. Technol.; 2011; vol. 26.
Young Gu Lee, et al; Thin-film encapsulation of top-emission organic . . . ; Organic Electronics; 2009; vol. 10; pp. 1352-1355.
International Search Report dated May 20, 2014.
International Search Report issued on May 20, 2014 for PCT/KR2013/009909 filed on Nov. 4, 2013.
Deokhyeon Kwon, Electrical properties of 4-mercaptophenol doped ZnO thin films prepared by atomic layer deposition; Dept. of Chemistry; The Graduate School; Hanyang University; 2013; pp. 1-50.

* cited by examiner

Fig. 19

| Acceleration time / Thin film | Initial | 24 hrs (1 day) | 120 hrs (5 days) | 360 hrs (15 days) | 720 hrs (30 days) |
|---|---|---|---|---|---|
| $Al_2O_3$ inorganic thin film | | | | | |
| Ca oxidation | 0 / 144 | 8 / 144 | 12 / 144 | 25 / 144 | 59 / 144 |
| $Al_2O_3$ / Al-4MP organic-inorganic hybrid super lattice thin film | | | | | |
| Ca oxidation | 0 / 144 | 0 / 144 | 0 / 144 | 1 / 144 | 1 / 144 |

ORGANIC-INORGANIC HYBRID THIN FILM AND METHOD FOR PRODUCING THE SAME

TECHNICAL FIELD

The present invention relates to an organic-inorganic hybrid thin film and a method for preparing the same and more specifically to an organic-inorganic hybrid thin film including a stable new functional group and a method for preparing the organic-inorganic hybrid thin film that is formed by the molecular layer deposition method alternately using inorganic precursor and organic precursor.

BACKGROUND TECHNOLOGY

Organic-inorganic hybrid materials are such materials that are able to exhibit both properties of an organic material and properties of an inorganic material by binding the organic material with the inorganic material based on a physical or chemical method.

The method that has been used the most to prepare the organic-inorganic hybrid thin film is the sol-gel method and it enables the easy preparation of organic-inorganic hybrid materials at low temperatures with the result that research thereon has been carried out extensively for a long time. Nevertheless, the sol-gel method has shortcomings such that it is difficult to control in terms of a monomolecular layer and that deformation occurs following thermal treatment, which makes it difficult to prepare an organic-inorganic hybrid thin film of high quality.

Another method for preparing the organic-inorganic hybrid thin film is based on intercalation and enables the preparation of the organic-inorganic hybrid material which was difficult to prepare by the sol-gel method. Nevertheless, because this method is also difficult to control in terms of a monomolecular layer and has slow deposition rates, it presents difficulties when preparing an organic-inorganic nano hybrid super-lattice of high quality.

The molecular self-assembly method prepares an organic-inorganic hybrid thin film by using static electricity and is a very useful method that enables polymer, nanoparticles, nanoplate, etc. to be grown in a layer form. Much effort is being spent on researching it. Nevertheless, the molecular self-assembly method prepares organic-inorganic hybrid thin films by using static electricity and does not represent technology that controls a monomolecular layer in a strict sense. Its low thermal stability makes it difficult to prepare a stable organic-inorganic hybrid thin film of high quality. In addition, the thermal deposition (evaporation) method prepares an organic-inorganic hybrid thin film in a gas phase and makes it difficult to control a monomolecular layer. In addition, its raw material molecules are very restricted so that its applications are also limited.

In order to solve such problems with the existing methods for preparing an organic-inorganic hybrid thin film, molecular layer deposition technology has been developed that enables not only organic polymers but also organic-inorganic hybrid materials to be deposited. The molecular layer deposition technology represents gas phase deposition in which inorganic or organic molecules can be controlled in a molecular unit based on the self-controlled surface reaction of inorganic or organic molecules. The S. M. George group as a representative example used the molecular layer deposition technology to prepare the alucone polymer film with trimethyl aluminium (TMA) and ethylene glycol (EG). However, in such existing molecular layer deposition, the functional group including an organic precursor has been restricted to a hydroxyl group, a carboxyl group and their derivatives and the organic-inorganic hybrid thin film prepared accordingly has a problem such that it becomes unstable and decomposed upon standing in the air.

In order to prevent characteristic deterioration of electronic devices etc. due to oxygen or moisture, development of a superior passivation film is in progress. Currently, the passivation film has various forms including the single film based on inorganic materials such as $SiO_2$, SiN and $Al_2O_3$, the multi-layered film prepared by alternately depositing inorganic materials, and the multi-layered film prepared by alternately depositing inorganic materials and organic materials. While ion beam deposition, electron beam deposition, plasma beam deposition and chemical vapour deposition have been used to form inorganic passivation films, such existing techniques have problems in that their deposition temperatures must be high and that coverage of a thin film was not excellent.

Thus the atomic layer deposition (ALD) method that enables the formation of a passivation film at low temperatures has been receiving much attention. ALD represents the ideal technology for preparing inorganic and metallic thin films in which a self-controlled reaction is used in an atomic unit to deposit a mono atomic layer and may be considered to be a deposition technique of a new concept that enables control of the thickness of a mono atomic layer. However, it has not achieved the desired performance yet because of the pin hole taking place during the process of passivation film formation.

DETAILED DESCRIPTION OF THE INVENTION

Technical Task

The present invention has as its objective to solve the problems with the prior art above and to provide a method for preparing a new organic-inorganic hybrid thin film in which a precursor compound used for forming an inorganic layer and a precursor compound used for forming an organic layer are alternately used.

The present invention also has as its objective to provide the organic-inorganic hybrid thin film prepared according to the preparation method of the present invention.

Means for Task Solution

The present invention provides the organic-inorganic hybrid thin film expressed by the formula 1 below to solve the tasks above.

$$—[M\text{-}X\text{-}R1\text{-}Y\text{-}]m— \qquad [\text{Formula 1}]$$

(In the formula 1 above m is 1 or more,

R1 is $C_{1-20}$ alkyl, $C_{5-20}$ cycloalkyl, or aryl or heteroaryl of 5~60 nuclear atoms, M is selected from a group consisting of Zn, Sn, In, Cd, Ga, Al, Ti, Si, V, Mn, Fe, Co, Cu, Zr, Ru, Mo, Nb and W, and X or Y is selected from a group consisting of O, S, N, NH and CO, and either X or Y is S.)

The organic-inorganic hybrid thin film according to the present invention characteristically has the thickness of 1 A to 50 A.

In the organic-inorganic hybrid thin film according to the present invention, assuming that the initial thickness of the organic-inorganic hybrid thin film is d0 and that the thickness of the organic-inorganic hybrid thin film after standing under the STP conditions for n hours is dn, the relation equation below is satisfied:

$$0 \leq (dn/d0) \leq 0.1 (0 \leq n \leq 240)$$

The present invention also provides a functional thin film comprising the organic-inorganic hybrid thin film according to the present invention; and an oxide layer of a metal selected from a group consisting of Zn, Sn, In, Cd, Ga, Al, Ti, Si, V, Mn, Fe, Co, Cu, Zr, Ru, Mo, Nb and W. The functional thin film may be a super-lattice thin film.

In the functional thin film comprising the organic-inorganic hybrid thin film according to the present invention, the thickness of the metal oxide layer ranges from 10 A to 2000 A.

In the functional thin film comprising the organic-inorganic hybrid thin film according to the present invention, assuming that the initial thickness of the functional thin film comprising the organic-inorganic hybrid thin film is D0 and that the thickness of the functional thin film comprising the organic-inorganic hybrid thin film after standing under the STP (standard temperature and pressure) conditions for n hours is Dn, the relation equation below is satisfied:

$$0 \leq (Dn/D0) \leq 0.1 (0 \leq n \leq 240)$$

The functional thin film according to the present invention is characteristically intended for an encapsulating application.

The present invention also provides a method for preparing an organic-inorganic hybrid thin film comprising, (1) a step in which the first precursor compound expressed by the formula 2 below is used to form an inorganic molecular layer; and $$M(R21)(R22) \ldots (R2n) \quad \text{[Formula 2]}$$

(In the Formula 2 above M is selected from a group consisting of Zn, Sn, Cd, Ti, Si, V, Mn, Fe, Co, Cu, Zr, Ru, Mo, Nb, W, In, Ga, Al and Tl
n is determined according to the oxidation number state of the metal M, and
R21 to R2n are each independently $C_{1-20}$ alkyl, $C_{1-20}$ alkoxide, a chloride group, a hydroxide group, an oxyhydroxide group, a nitrate group, a carbonate group, an acetate group or an oxalate group.)

(2) a step in which the second precursor compound expressed by the formula 3 below is reacted with the inorganic molecular layer to form an organic molecular layer over the inorganic molecular layer.

$$R3\text{-}S\text{-}R4\text{-}R5 \quad \text{[Formula 3]}$$

(In the Formula 3 above R3 is hydrogen, COR6, $C_{1-20}$ alkyl, $C_{5-20}$ cycloalkyl, or aryl or heteroaryl of 5~60 in the nuclear atoms,
R4 is $C_{1-20}$ alkyl, $C_{5-20}$ cycloalkyl, or aryl or heteroaryl of 5~60 nuclear atoms,
R5 is one or more species selected from a group consisting of a $C_{1-20}$ alkoxy group, an ether group, a carboxylic group, COR6, a thiol group and an amine group, and
R6 is one or more species selected from a group consisting of hydrogen, an alkoxy group, an ether group, a carboxylic group, a thiol group, and an amine group.)

In the method for preparing the organic-inorganic molecular film according to the present invention, the first precursor compound is reacted with a substrate to form an inorganic layer on the substrate surface.

The first precursor compound can be any precursor that enables an inorganic thin film to be formed, and a metallic compound having high vapour pressure is used to inject a desired amount of the precursor into a chamber in a short period. For example, the first precursor compound can be a group consisting of alkoxide, chloride, hydroxide, oxyhydroxide, nitrate, carbonate, acetate, oxalate and their mixtures that includes one species of a metal selected from a group consisting of Zn, Sn, In, Cd, Ga, Al, Ti, Si, V, Mn, Fe, Co, Cu, Zr, Ru, Mo, Nb and W and their combinations as the metal M.

The first precursor compound characteristically comprises n substituents of R21, R22 . . . R2n that are determined according to the oxidation number state of the metal M wherein R21 to R2n are each independently $C_{1-20}$ alkyl, $C_{1-20}$ alkoxide, a chloride group, a hydroxide group, an oxyhydroxide group, a nitrate group, a carbonate group, an acetate group or an oxalate group.

Specifically, raw material gases used for forming the inorganic layer including a Zn metal include DEZn (diethyl zinc), and DMZn (dimethyl zinc), while the raw material gases used for forming the inorganic layer including an Al metal can be trimethyl aluminium (TMA), triethyl aluminium (TEA), etc.

In the method for preparing the organic-inorganic hybrid thin film according to the present invention, SR3 or R5 of the second precursor compound expressed by the formula 3 above reacts with the inorganic layer formed on the substrate surface by the first precursor compound to form an organic-inorganic hybrid thin film.

In the method for preparing the organic-inorganic hybrid thin film according to the present invention, the compound expressed by the formula 4 can be used for the second precursor compound.

[Formula 4]

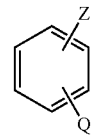

(In the formula 4, Z is a thiol group, Q is any one selected from a thiol group and a hydroxyl group, and Z and Q are located at the ortho, meta or para position.)

In the method for preparing the organic-inorganic hybrid thin film according to the present invention, the compound expressed by the formula 5 or formula 6 below can be used for the second precursor compound.

[Formula 5]

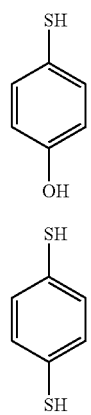

[Formula 6]

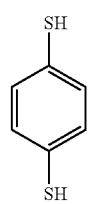

In the method for preparing the organic-inorganic hybrid thin film according to the present invention, the step (1) and step (2) can be repeatedly performed to form the organic-inorganic hybrid thin film at a desired thickness.

In the method for preparing the organic-inorganic hybrid thin film according to the present invention, the substrate is selected from a group consisting of glass, silicon and plastic.

The method for preparing the organic-inorganic hybrid thin film according to the present invention further includes a step in which an oxide layer is formed over the substrate surface prior to step (1).

The present invention also provides a method for preparing a super-lattice thin film comprising an organic-inorganic hybrid thin film that further includes a step (3) in which an oxide layer of a metal selected from a group consisting of Zn, Sn, In, Cd, Ga, Al, Ti, Si, V, Mn, Fe, Co, Cu, Zr, Ru, Mo, Nb and W is formed by atomic layer deposition after an organic-inorganic hybrid thin film is formed by step (1) and step (2).

In the method for preparing a super-lattice thin film according to the present invention, step (3) is repeatedly performed n2 times (n2 is 1 or more) after each of steps (1) and (2) has repeatedly been performed n1 times (n1 is 1 or more).

In the method for preparing a super-lattice thin film according to the present invention, the steps (1) to (3) are repeatedly performed.

Effects of the Invention

Because the organic-inorganic hybrid thin film and encapsulting film according to the present invention include a new functional group so as to remain stable in air, they can be applied to various fields including nano patterning for manufacturing semiconductor and electronic devices, chemical sensors and biosensors, nano tribology, surface modification, nano electronic machine systems (NEMS), micro electronic machine systems (MEMS) and non-volatile memory.

The method for preparing the organic-inorganic hybrid thin film according to the present invention enables provision of a very stable organic-inorganic hybrid multi-layered molecular film in air by including a new functional group not used previously in its organic precursor when preparing the organic-inorganic hybrid thin film by alternately using inorganic precursor and organic precursor according to the molecular layer deposition method.

BRIEF DESCRIPTION OF THE DRAWINGS

FIG. 19 shows results of the Ca test on the organic-inorganic hybrid thin film prepared in one example of the present invention and the thin film prepared in the comparative example.

SPECIFIC DETAILS FOR IMPLEMENTING THE INVENTION

The present invention is described in further detail below according to examples of the present invention. However, the present invention is not limited to the examples below.

Example 1

After an Si (100) substrate was washed with distilled water and acetone, it was purged with $N_2$ as 2-3 times to remove any contaminants on the substrate surface before diethyl zinc (DEZn) was used as a first precursor compound to deposit a diethyl zinc (DEZn) thin film over the Si substrate according to the molecular layer deposition method.

Over the diethyl zinc (DEZn) thin film was formed an organic molecular film by using 4-mercapto phenol as a second precursor compound according to the molecular layer deposition method to prepare an organic-inorganic hybrid thin film. Argon was used for both carrier gas and purging gas, and DEZn and 4-mercapto phenol were respectively evaporated at 20° C. and 70° C. One cycle was achieved by exposure to DEZn for 2 seconds, purging with Ar for 10 seconds, exposure to 4-mercapto phenol for 2 seconds and purging with Ar for 50 seconds. The thin film was grown at a temperature of 80° C. to 200° C. and under a pressure of 300 mTorr.

Experiment

Figure 1:
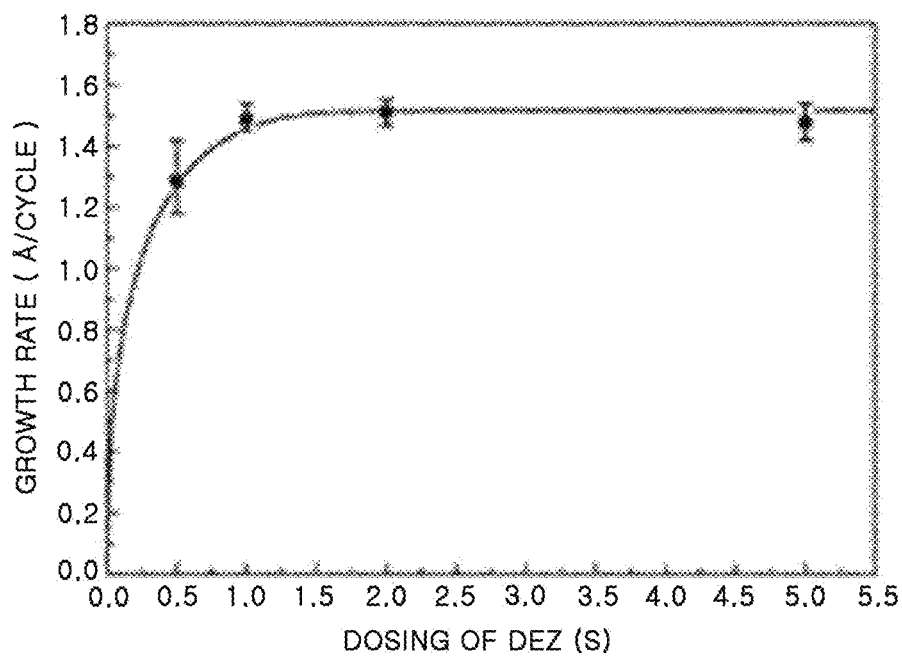
FIG. 1 and FIG. 2 respectively show thin film growth rates versus the injection amounts of first precursor and second precursor in one example of the present invention.
Figure 2:
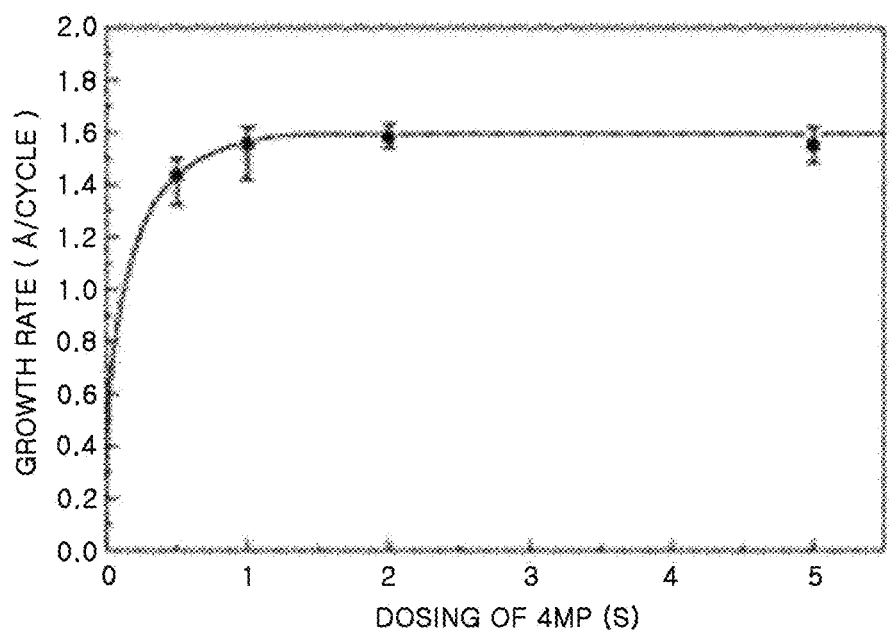

Measurement of Growth Rates Versus Injection Time of Organic Precursor and Inorganic Precursor In Example 1, growth rates of the thin film according to the injection time of the first precursor compound of diethyl zinc (DEZn) and growth rates of the thin film according to the injection time of the second precursor compound of 4-mercapto phenol were measured and respectively shown in FIG. 1 and FIG. 2.

It may be noted from FIG. 1 and FIG. 2 that growth rates of the thin films increased with injection amounts of the first precursor compound of diethyl zinc (DEZn) and the second precursor compound of 4-mercapto phenol and then the growth rates no longer increased but remained at certain rates.

Experiment

IR Spectroscopic Measurement

Figure 3:
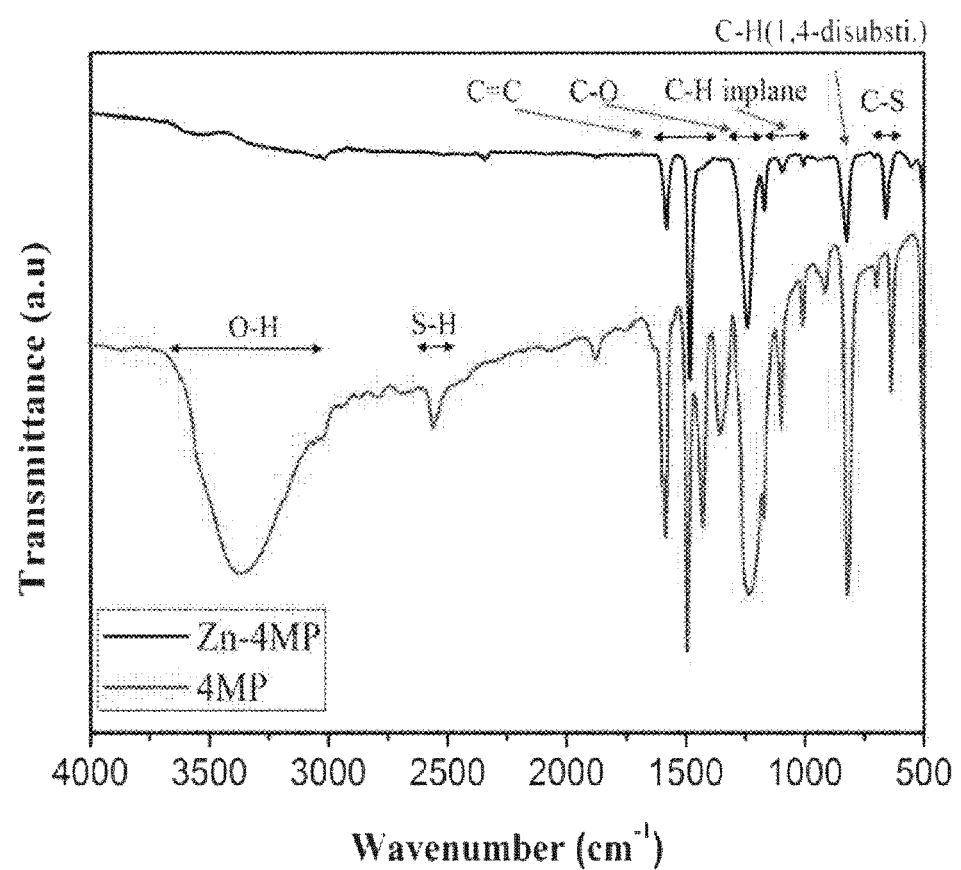
FIG. 3 shows results of the ultraviolet spectroscopic measurement on the organic-inorganic hybrid thin film and 4-mercapto phenol prepared in one example of the present invention.

IR spectroscopic measurements were made on the organic-inorganic hybrid thin film prepared by the same method as Example 1 except that KBr pellets were used instead of the Si substrate and 4-mercapto phenol, and the results are shown in FIG. 3.

It may be verified in FIG. 3 that a hydroxyl group and a thiol group of 4-mercapto phenol are found in the comparative example in which only 4-mercapto phenol is included whereas in the case of the organic-inorganic hybrid thin film according to the present invention, the hydroxyl group and the thiol group of mercapto phenol used as its second precursor react with the inorganic molecular layer prepared by its first precursor to form a hybrid thin film so that the hydroxyl group and thiol group of mercapto phenol are not detected by the infrared spectroscopic method.

Experiment

UV-VIS Spectroscopic Measurement

Figure 4:
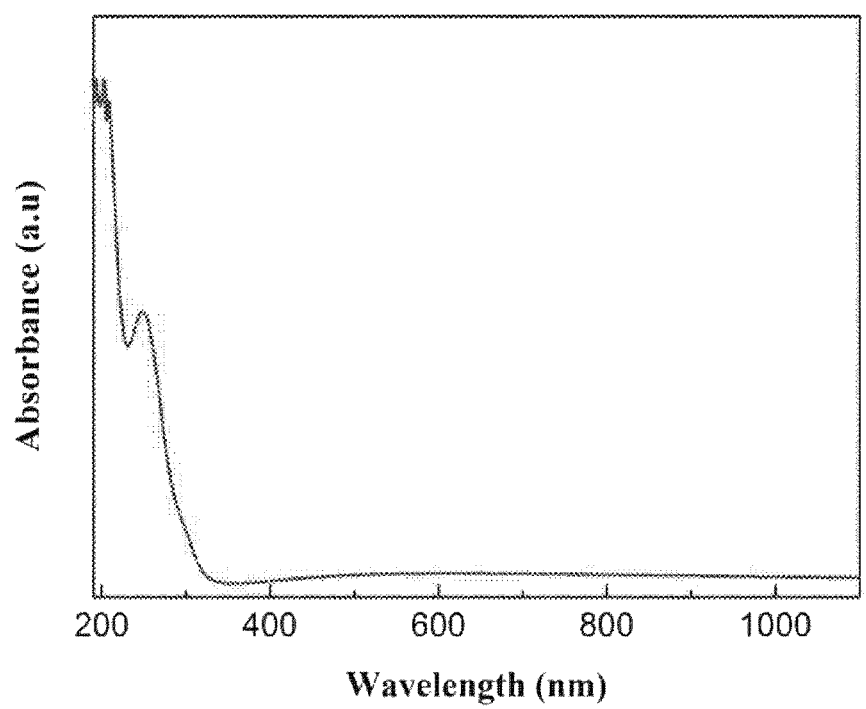
FIG. 4 shows results of the UV-Vis absorption measurement on the organic-inorganic hybrid thin film prepared in one example of the present invention.

UV-Vis absorption on the organic-inorganic hybrid thin film prepared in Example 1 above was measured and the results are shown in FIG. 4.

It may be verified from FIG. 4 that the organic-inorganic hybrid thin film according to the present invention has no absorption in the visible ray range.

Comparative Example

In a comparative example an organic-inorganic hybrid thin film was prepared the same way as in Example 1 above except that diethyl zinc (DEZn) was used as its first precursor compound to deposit a diethyl zinc (DEZn) thin film oven an Si substrate according to the molecular layer deposition method and then hydroquinone (HQ) was used as its second precursor compound.

Experiment

Stability Test in Air

Figure 5:
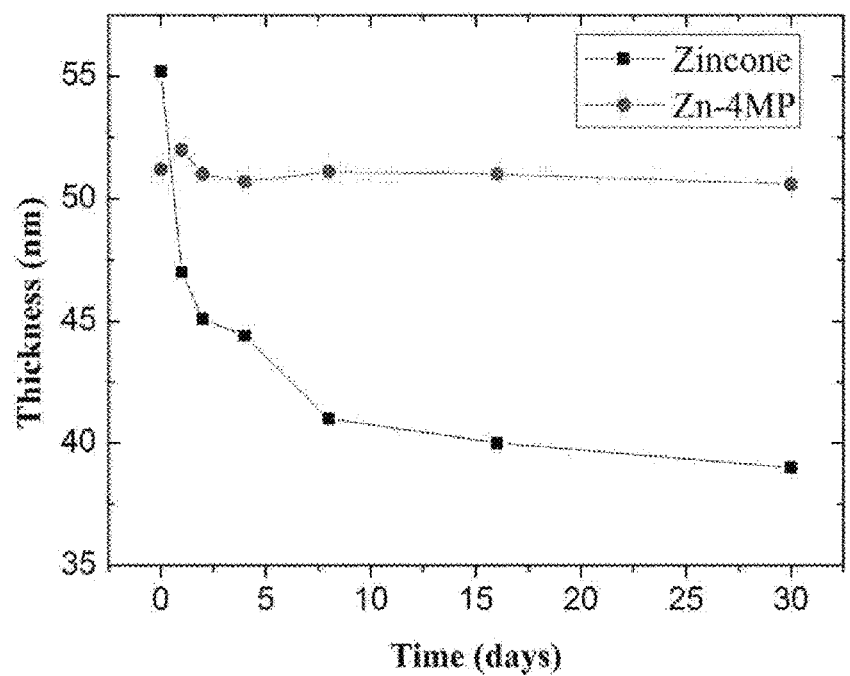
FIG. 5 shows results of the air stability test on the organic-inorganic hybrid thin film prepared in one example of the present invention and the thin film prepared in the comparative example.

While the organic-inorganic hybrid thin film of Example and the organic-inorganic hybrid thin film prepared in the Comparative Example above were left in air, changes in their thicknesses were measured to test stability in air, and the results are shown in FIG. 5.

It may be realized in FIG. 5 that unlike in the present invention the thickness drastically decreases in the case of the Comparative Example that does not include an S group whereas the thickness does not change with time in the case of the Example according to the present invention and that the organic-inorganic hybrid multi-layered film including an S group is very stable in air.

Example 2

Figure 6:
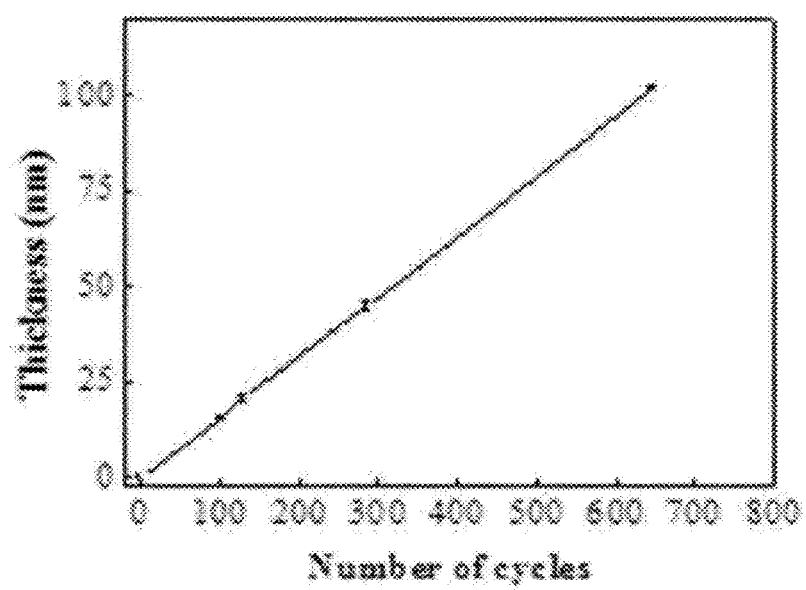
FIG. 6 shows results of the thin film thickness measurement versus the cycle of the organic-inorganic hybrid thin film formation process in one example of the present invention.

As in Example 1 above, diethyl zinc (DEZn) was used as the first precursor compound to deposit a thin film over an Si substrate and 4-mercapto phenol was used as the second precursor compound to form an organic-inorganic hybrid thin film over the diethyl zinc (DEZn) thin film according to the molecular layer deposition method before the process of forming the diethyl zinc (DEZn) by the first precursor compound, and while the thin film based on the second precursor compound was repeatedly formed, thicknesses of the thin film were measured and the results are shown in FIG. 6.

It may be verified in FIG. 6 that the number of repetitions for the process of forming the thin film by the first precursor compound and forming the thin film by the second precursor compound is proportional to the thickness of the thin film formed.

Experiment

Surface Roughness Measurement

Figure 7:
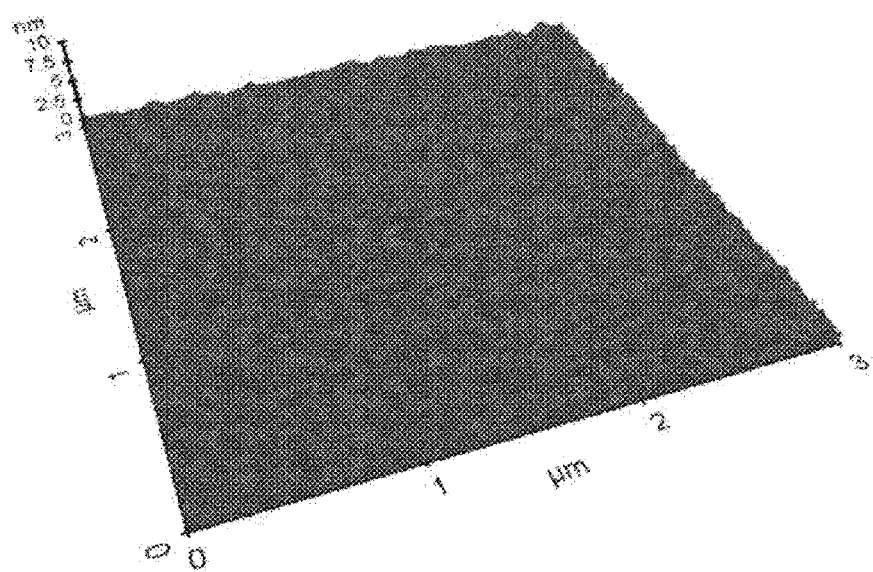
FIG. 7 shows results of the surface roughness measurement on the hybrid thin film prepared in one example of the present invention.

The organic-inorganic hybrid thin film of 50 nm in the thickness prepared in Example 2 was measured for its surface roughness with AFM, and the results are shown in FIG. 7. The average roughness measured was 2.2 A.

Example 3

After an Si (100) substrate was washed with distilled water and acetone, it was purged with $N_2$ gas 2-3 times to remove any contaminants on the substrate surface before trimethyl aluminium (TMA) was used as a first precursor compound to deposit a trimethyl aluminium (TMA) thin film over the Si substrate according to the molecular layer deposition method.

Over the trimethyl aluminium (TMA) thin film was formed an organic molecular film by using 4-mercapto phenol as a second precursor compound according to the molecular layer deposition method to prepare an organic-inorganic hybrid thin film.

Argon was used for both carrier gas and purging gas, and DEZn and 4-mercapto phenol were respectively evaporated at 20° C. and 70° C. One cycle was achieved by exposure to DEZn for 2 seconds, purging with Ar for 10 seconds, exposure to 4-mercapto phenol for 2 seconds and purging with Ar for 50 seconds. The thin film was grown at the temperature of 80° C. to 200° C. and under a pressure of 300 mTorr.

Experiment

Figure 8:
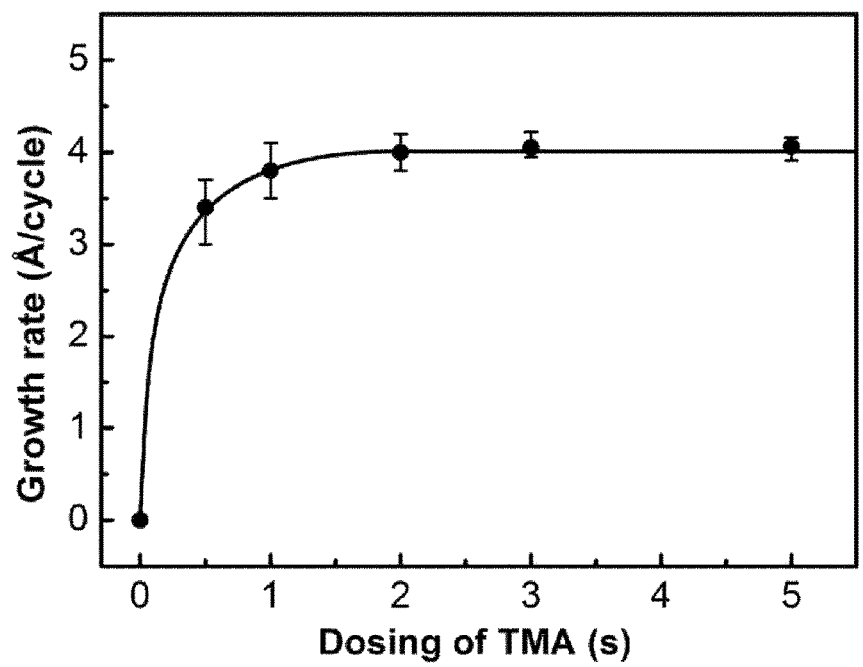
FIG. 8 and FIG. 9 respectively show thin film growth rates versus the injection amounts of first precursor and second precursor in one example of the present invention.
Figure 9:
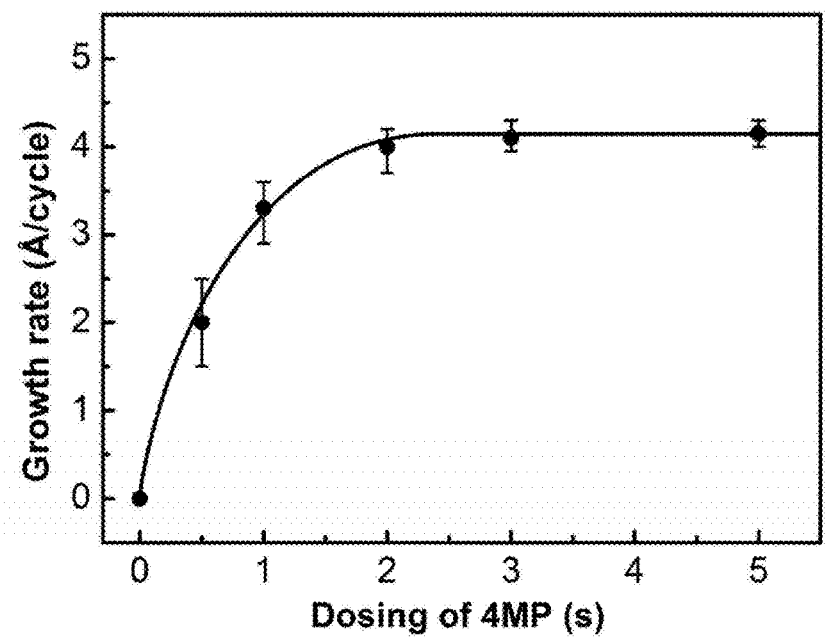

Measurement of Growth Rates Versus Injection Time of Organic Precursor and Inorganic Precursor In Example 3, growth rates of the thin film according to the injection time of the first precursor compound of trimethyl aluminium (TMA) and growth rates of the thin film according to the injection time of the second precursor compound of 4-mercapto phenol were measured and respectively shown in FIG. 8 and FIG. 9.

It may be noted from FIG. 8 and FIG. 9 that growth rates of the thin films increased with injection amounts of the first precursor compound of trimethyl aluminium (TMA) and the second precursor compound of 4-mercapto phenol and then the growth rates no longer increased but remained at certain rates.

Experiment

IR Spectroscopic Measurement

Figure 10:
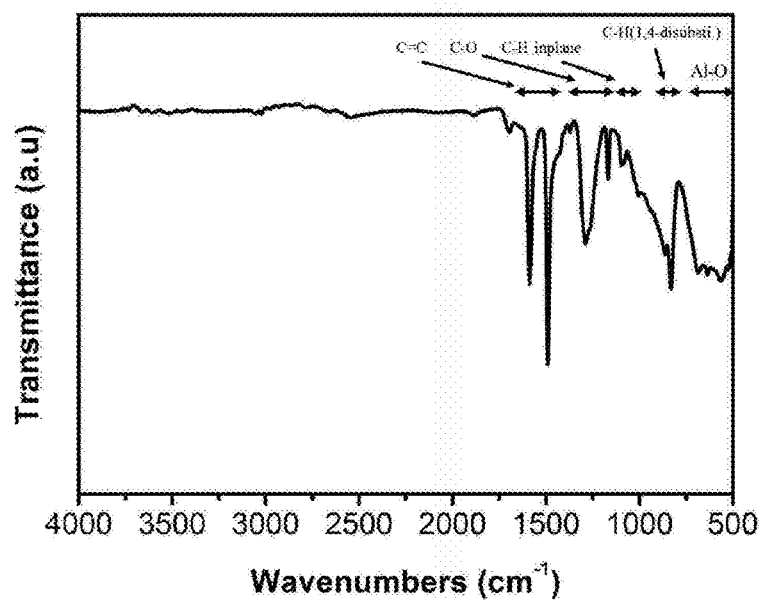
FIG. 10 shows results of the ultraviolet spectroscopic measurement on the organic-inorganic hybrid thin film prepared in one example of the present invention.

IR spectroscopic measurements were made on the organic-inorganic hybrid thin film prepared by the same method of Example 3 except that KBr pellets were used instead of the Si substrate and 4-mercapto phenol, and the results are shown in FIG. 10.

It may be verified in FIG. 10 that in the case of the organic-inorganic hybrid thin film according to the present invention, the hydroxyl group and the thiol group of mercapto phenol used as its second precursor react with the inorganic molecular layer prepared by its first precursor to form a hybrid thin film so that the hydroxyl group and the thiol group of mercapto phenol are not detected by the infrared spectroscopic method.

Experiment

UV-VIS Spectroscopic Measurement

Figure 11:
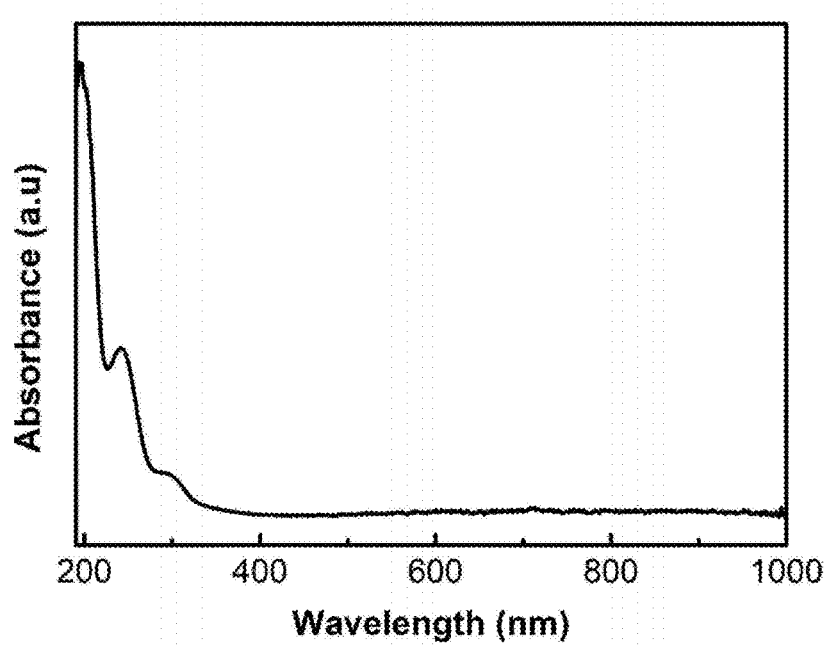
FIG. 11 shows results of the UV-Vis absorption measurement on the organic-inorganic hybrid thin film prepared in one example of the present invention.

UV-Vis absorption on the organic-inorganic hybrid thin film prepared in Example 3 above was measured and the results are shown in FIG. 11.

It may be verified from FIG. 11 that the organic-inorganic hybrid thin film according to the present invention has no absorption in the visible ray range.

Comparative Example

In a comparative example an organic-inorganic hybrid thin film was prepared in the same way as in Example 3 above except that trimethyl aluminium (TMA) was used as its first precursor compound to deposit a trimethyl aluminium (TMA) thin film oven an Si substrate according to the molecular layer deposition method and then hydroquinone (HQ) was used as its second precursor compound.

Experiment

Stability Test in Air

Figure 12:
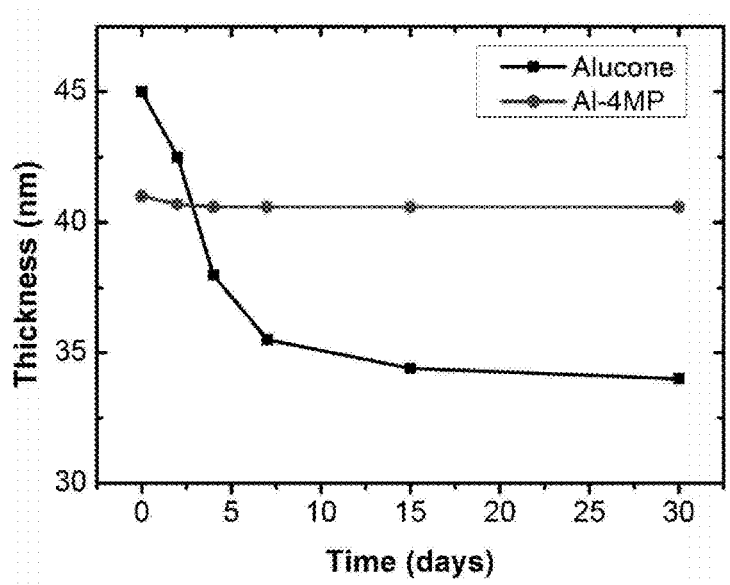
FIG. 12 shows results of the air stability test on the organic-inorganic hybrid thin film prepared in one example of the present invention and the thin film prepared in the comparative example.

While the organic-inorganic hybrid thin film of Example and the organic-inorganic hybrid thin film prepared in the Comparative Example above were left in air, changes in their thicknesses were measured to test stability in air, and the results are shown in FIG. 12.

It may be recognized in FIG. 12 that, assuming that the initial thickness is d0 and the thickness in n hours is dn, dn/d0 in the case of the Comparative Example without including the S group increases to 0.5 or more as a result of a drastic decrease in its thickness unlike in the present invention whereas in the case of the Example according to the present invention, dn/d0 is kept at 0.1 or less as a result of the absence of changes in its thickness with time and that the organic-inorganic hybrid thin film according to the present invention is very stable in air.

Example 4

Figure 13:
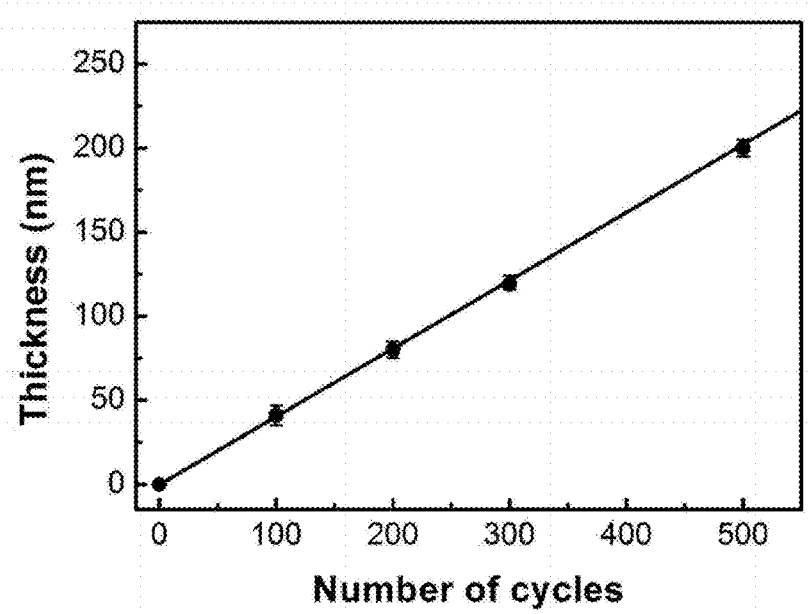
FIG. 13 shows results of the thin film thickness measurement of the organic-inorganic hybrid thin film formation process in one example of the present invention.

As in Example 3 above, trimethyl aluminium (TMA) was used as the first precursor compound to deposit a thin film over an Si substrate and 4-mercapto phenol was used as the second precursor compound to form an organic-inorganic hybrid thin film over the trimethyl aluminium (TMA) thin film according to the molecular layer deposition method before the process of forming the trimethyl aluminium (TMA) thin film by the first precursor compound, and while the thin film based on the second precursor compound was repeatedly formed, thicknesses of the thin film were measured and the results are shown in FIG. 13.

It may be verified in FIG. 13 that the number of repetitions for the process of forming the thin film by the first precursor compound and forming the thin film by the second precursor compound is proportional to the thickness of the thin film formed.

Experiment

Surface Roughness Measurement

Figure 14:
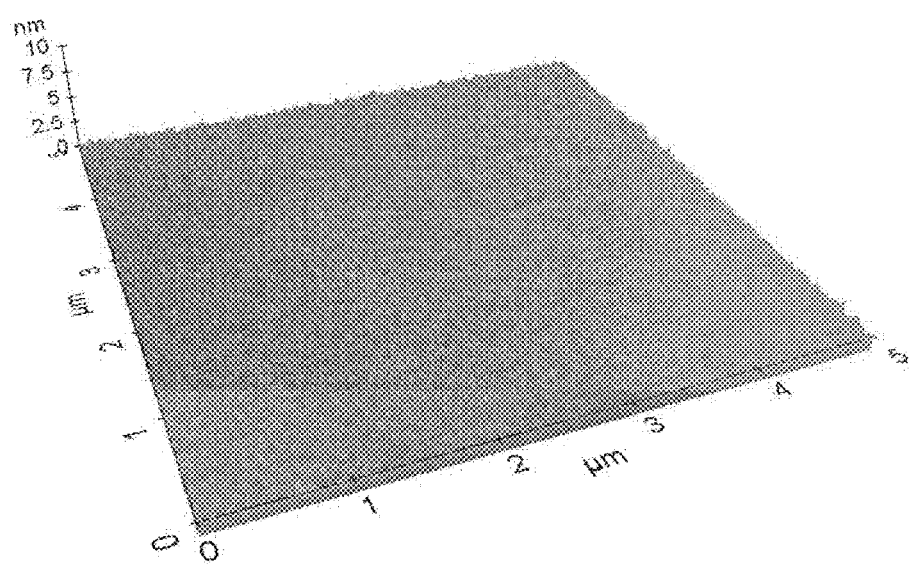
FIG. 14 shows results of the surface roughness measurement on the hybrid thin film prepared in one example of the present invention.

The organic-inorganic hybrid thin film of 50 nm in the thickness prepared in Example 4 was measured for its surface roughness with AFM, and the results are shown in FIG. 14. The average roughness measured was 2.8 A.

Example 5

After an organic-inorganic hybrid thin film was prepared in the same way as in Examples 1 and 3 above, an $Al_2O_3$ thin film was deposited over the organic-inorganic hybrid thin film according to the atomic layer deposition method, and such a process was repeated by controlling the ratio of the $Al_2O_3$ thin film based on atomic layer deposition to the organic-inorganic hybrid thin film according to the present invention to prepare an organic-inorganic hybrid functional thin film.

In order to form the $Al_2O_3$ thin film according to atomic layer deposition, argon gas was used as carrier gas and purging gas, and trimethyl aluminium (TMA) and $H_2O$ were evaporated at normal temperature. Its cycle was achieved by exposure to TMA for 1 second, purging with Ar for 5 seconds, exposure to $H_2O$ for 1 second and purging with Ar for 5 seconds. The above thin film was grown at a temperature of 80° C. under a pressure of 300 mTorr.

Experiment

TEM Measurement

Figure 15:
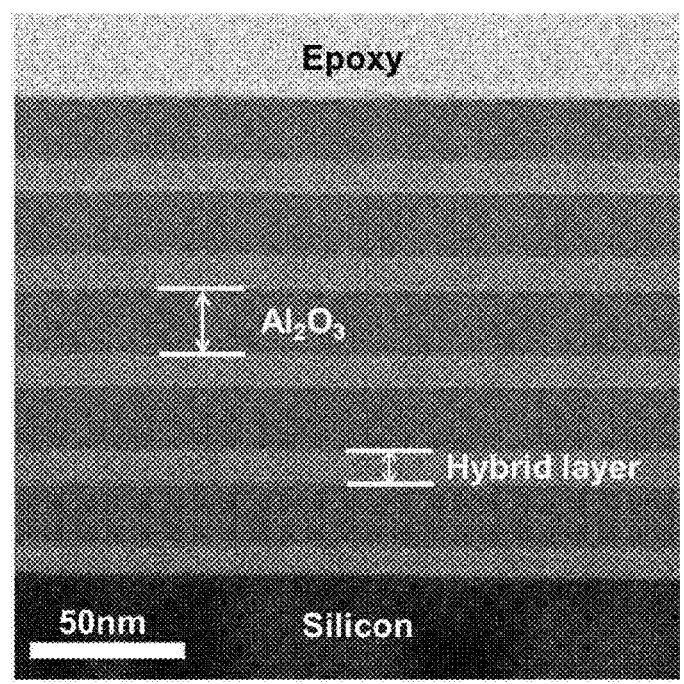
FIG. 15 shows results of the TEM photograph measurement on the organic-inorganic hybrid super-lattice thin film prepared in one example of the present invention.

The TEM photograph was measured when the ratio of the organic-inorganic hybrid thin film:$Al_2O_3$ thin film prepared in Example 5 above was 1:2, and the results are shown in FIG. 15. It may be verified in Figure that the $Al_2O_3$ thin film according to atomic layer deposition and the organic-inorganic hybrid thin film according to the present invention were alternately formed.

Experiment

Measurement of Pinhole Formation Inhibition Effects

Figure 16:
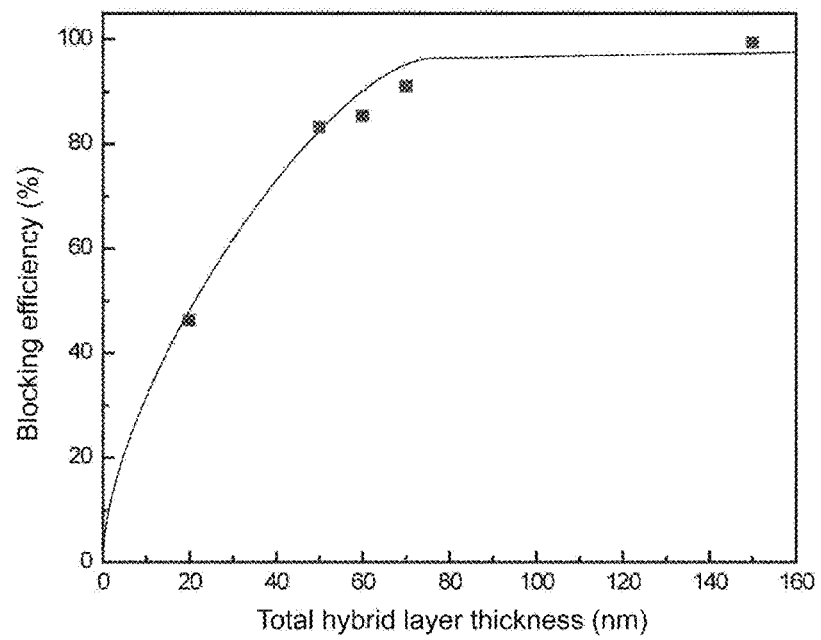
FIG. 16 and FIG. 17 show the rate of pinhole formation inhibition measured by varying the thickness of an organic-inorganic hybrid thin film in the organic-inorganic hybrid super-lattice thin film prepared in one example of the present invention.
Figure 17:
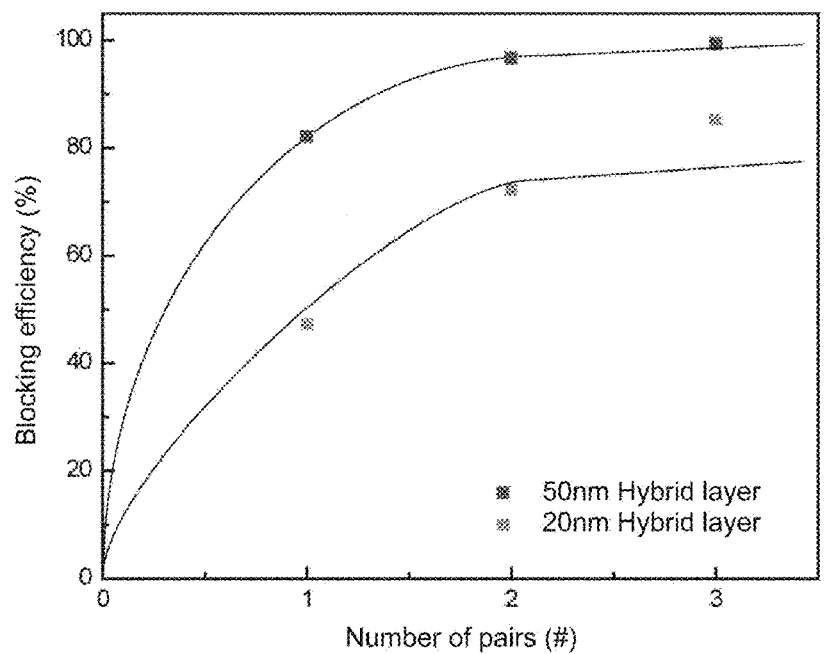

In Example 5 above, rates of pinhole formation inhibition were measured by varying the thickness of the organic-inorganic hybrid thin film, and the results are shown in FIG. 16 and FIG. 17.

It may be realized in FIG. 16 that pinholes are seldom formed if the thickness of the organic-inorganic hybrid thin film according to the present invention is 80 nm or more.

Experiment

Thin Film Stress Measurement

Figure 18:
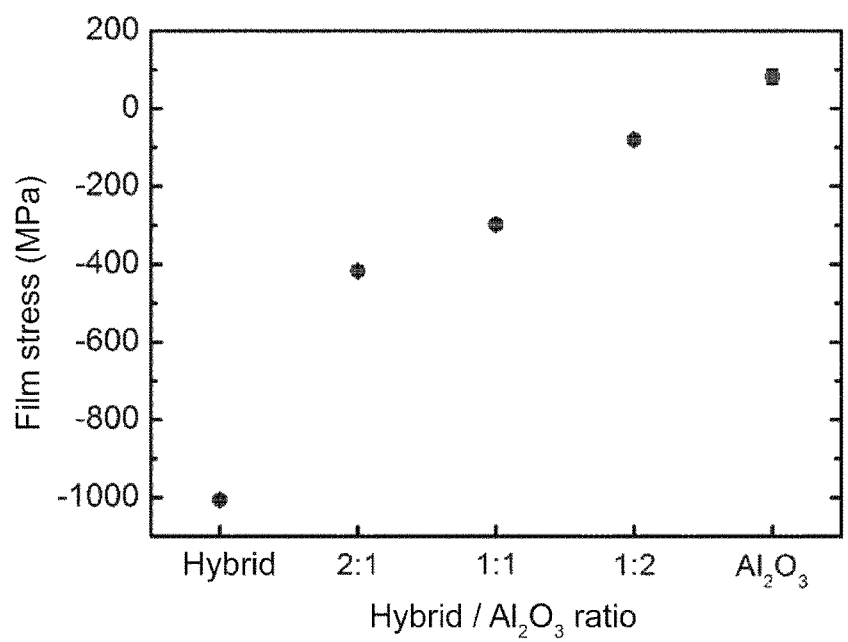
FIG. 18 shows results of the thin film stress measurement versus the ratio of the $Al_2O_3$ thin film formed by atomic layer deposition to the organic-inorganic hybrid thin film in the organic-inorganic hybrid super-lattice thin film prepared in one example of the present invention.

In the organic-inorganic hybrid functional thin film prepared in Example 5 above, thin film stress was measured versus the ratio of the $Al_2O_3$ thin film to the organic-inorganic hybrid thin film according to the present invention while the total thickness of the thin film was kept the same, and the results are shown in FIG. 18.

Experiment

Measurements of Moisture Permeability Resistance and Oxygen Permeability Resistance The organic-inorganic hybrid functional thin film prepared in Example 5 above, and the $Al_2O_3$ thin film of the Comparative Example were measured for their moisture permeability resistance and oxygen permeability resistance, and the results are listed in Table 1 and FIG. 19 below.

It may be noted from Table 1 and FIG. 19 below that the functional thin film comprising the organic-inorganic hybrid thin film and $Al_2O_3$ according to the present invention has superior moisture permeation resistance and oxygen permeation resistance to those of the Comparative Example.

TABLE 1

| Barrier Film (nm) | WVTR (g/m²day) | OTR (cm³/m²day) |
|---|---|---|
| $Al_2O_3$ (100 nm) | $3.11 \times 10^{-2}$ | $0.66 \times 10^{-5}$ |
| Organic/$Al_2O_3$ superlattice (100 nm) | $3.68 \times 10^{-7}$ | $8.33 \times 10^{-5}$ |

INDUSTRIAL VIABILITY

Because the organic-inorganic hybrid thin film and encapsulting film according to the present invention include a new functional group so as to remain stable in air, they can be applied to various fields including nanos patterning for manufacturing semiconductors and electronic devices, chemical sensors and biosensors, nano tribology, surface modification, nano electronic machine systems (NEMS), micro electronic machine systems (MEMS) and non-volatile memory.

The method for preparing the organic-inorganic hybrid thin film according to the present invention enables provision of a very stable organic-inorganic hybrid multi-layered molecular film in air by including a new functional group not used previously in its organic precursor when preparing the organic-inorganic hybrid thin film by alternately using inorganic precursor and organic precursor according to the molecular layer deposition method.

We claim:

1. A hybrid organic/inorganic thin film, represented by Formula 1:

$$[M\text{-}X\text{-}R1\text{-}Y\text{-}]m\text{-} \quad \text{[Formula 1]}$$

where
m is 1 or more,
R1 is a substituted or an unsubstituted $C_{1-20}$ alkyl, $C_{5-20}$ cycloalkyl, or aryl or heteroaryl with an atomic number of 5-60,
M is selected from the group consisting of Zn, Sn, In, Cd, Ga, Al, Ti, Si, V, Mn, Fe, Co, Cu, Zr, Ru, Mo, Nb, and W,
X and Y are each selected from the group consisting of O, S, N, NH and CO, and
one of X and Y is S.

2. The hybrid organic/inorganic thin film in of claim 1, which has a thickness of 1 Å to 500 Å.

3. The hybrid organic/inorganic thin film of claim 1, wherein when an initial thickness of the hybrid organic/inorganic thin film is d0 and a thickness of the hybrid organic/inorganic thin film after standing under STP conditions for n hours is dn, the following relationship is satisfied:

$$(dn/d0) \leq 0.1 \text{ where } 0 \leq n \leq 240.$$

4. A functional thin film, comprising:
the hybrid organic/inorganic thin film of claim 1; and
an oxide layer of a metal selected from the group consisting of Zn, Sn, In, Cd, Ga, Al, Ti, Si, V, Mn, Fe, Co, Cu, Zr, Ru, Mo, Nb, and W.

5. The functional thin film of claim 4, wherein a thickness of the oxide layer ranges from 10 Å to 2000 Å.

6. The functional thin film of claim 4, wherein, when an initial thickness of the functional thin film is D0 and a thickness of the functional thin film after standing under STP conditions for n hours is Dn, the following relationship is satisfied:

$$0 \leq (Dn/D0) \leq 0.1 \text{ where } 0 \leq n \leq 240.$$

7. The functional thin film of claim 4, which is suitable for encapsulation.

8. A method for preparing a hybrid organic/inorganic thin film, the method comprising:
(1) forming an inorganic molecular layer on a surface of a substrate using a first precursor compound of Formula 2:

$$M(R21)(R22) \ldots (R2n) \quad \text{[Formula 2]}$$

where M is a metal selected from the group consisting of Zn, Sn, Cd, Ti, Si, V, Mn, Fe, Co, Cu, Zr, Ru, Mo, Nb, W, In, Ga, Al, and Tl,
n is determined according to an oxidation number state of the metal M, and
R21 to R2n are each independently $C_{1-20}$ alkyl, $C_{1-20}$ alkoxide, a chloride group, a hydroxyl group, an oxyhydroxide group, a nitrate group, a carbonate group, an acetate group or an oxalate group, and
(2) forming an organic molecular layer on the inorganic molecular layer via a reaction of a second precursor compound of Formula 3 with the inorganic molecular layer:

$$R3\text{-}S\text{-}R4\text{-}R5 \quad \text{[Formula 3]}$$

where R3 is hydrogen, COR6, $C_{1-20}$ alkyl, $C_{5-20}$ cycloalkyl, or aryl or heteroaryl with an atomic number of 5-60,
R4 is $C_{1-20}$ alkyl, $C_{5-20}$ cycloalkyl, or aryl or heteroaryl with an atomic number of 5-60, R5 is at least one selected from the group consisting of a $C_{1-20}$ alkoxy group, an ether group, a carboxyl group, COR6, a thiol group, and an amine group, and R6 is at least one selected from the group consisting of hydrogen, an alkoxy group, an ether group, a carboxyl group, a thiol group, and an amine group.

9. The method of claim 8, wherein the second precursor compound is represented by formula 4:

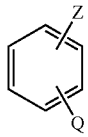

[Formula 4]

where Z is a thiol group, Q is a thiol group or a hydroxyl group, and Z and Q are located at the ortho, meta or para position.

10. The method of claim 8, wherein the second precursor compound is represented by formula 5:

[Formula 5]

11. The method of claim 8, wherein the second precursor compound is represented by formula 6:

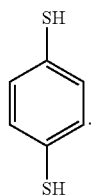

[Formula 6]

12. The method of claim 8, further comprising
repeatedly performing the forming (1) and the forming (2).

13. The method of claim 8, wherein the substrate is selected from the group consisting of glass, silicon and plastic.

14. The method of claim 8, further comprising:
forming an oxide layer on the surface of the substrate prior to the forming (1).

15. The method of claim 8, further comprising:
(3) forming an oxide layer of a metal selected from the group consisting of Zn, Sn, In, Cd, Ga, Al, Ti, Si, V, Mn, Fe, Co, Cu, Zr, Ru, Mo, Nb, and W by atomic layer deposition
wherein when an initial thickness of the hybrid organic/inorganic thin film is d0 and a thickness of the hybrid organic/inorganic thin film after standing under STP conditions for n hours is dn, the following relationship is satisfied:

$0 \leq (dn/d0) \leq 0.1$, where $0 \leq n \leq 240$.

16. The method of claim 15, wherein the forming (3) is repeatedly performed n2 times where n2 is 1 or more after repeatedly performing the forming (1) and the forming (2) n1 times where n1 is 1 or more.

17. The method of claim 15, wherein the forming (1), the forming (2), and the forming (3) are repeatedly performed.

* * * * *

UNITED STATES PATENT AND TRADEMARK OFFICE
CERTIFICATE OF CORRECTION

PATENT NO. : 9,576,876 B2
APPLICATION NO. : 14/413754
DATED : February 21, 2017
INVENTOR(S) : Myung Mo Sung et al.

Page 1 of 1

It is certified that error appears in the above-identified patent and that said Letters Patent is hereby corrected as shown below:

On the Title Page

Item (71), the applicants information is out of order. Item (71) should read:
-- (71) Applicants: BASF Coatings GmbH, Muenster (DE),
   IUCF-HYU (INDUSTRY-UNIVERSITY COOPERATION FOUNDATION HANYANG UNIVERSITY), Seongdong-gu (KR) --

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*